United States Patent [19]
Theissen

[11] 3,941,830
[45] Mar. 2, 1976

[54] SUBSTITUTED PHENOXYBENZOIC ACIDS AND ESTERS THEREOF
[75] Inventor: Robert J. Theissen, Westfield, N.J.
[73] Assignee: Mobil Oil Corporation, New York, N.Y.
[22] Filed: Sept. 19, 1973
[21] Appl. No.: 398,610

Related U.S. Application Data
[63] Continuation of Ser. No. 114,712, Feb. 11, 1971, Pat. No. 3,784,635, which is a continuation-in-part of Ser. No. 819,412, April 25, 1969, Pat. No. 3,652,645.

[52] U.S. Cl. .......................... 260/471 R; 260/520 E
[51] Int. Cl.² .................. C07C 69/78; C07C 79/46
[58] Field of Search ...................... 260/471 R, 520

[56] References Cited
UNITED STATES PATENTS
3,798,276   3/1974   Bayer et al. .................... 260/471 R Primary Examiner—Richard L. Raymond
Attorney, Agent, or Firm—Charles A. Huggett; Hastings S. Trigg

[57] ABSTRACT
2-Nitro-5-(substituted-phenoxy)benzoic acids and esters salts, amides, and acyl halides thereof comprise a class of compounds that are highly effective herbicides.

5 Claims, No Drawings

SUBSTITUTED PHENOXYBENZOIC ACIDS AND ESTERS THEREOF

CROSS-REFERENCE TO RELATED APPLICATIONS

This application is a continuation of copending application Ser. No. 114,712, filed Feb. 11, 1971, now U.S. Pat. No. 3,784,635 which is a continuation-in-part of application Ser. No. 819,412, filed Apr. 25, 1969, now U.S. Pat. No. 3,652,645.

BACKGROUND OF THE INVENTION

1. Field of the Invention

This invention is concerned with certain phenoxybenzoic acid compounds and their use as herbicides.

2. Description of the Prior Art

It has been proposed to use as herbicides 2-methoxybenzoic acids (U.S. Pat. No. 3,013,054) and 4-phenoxybenzoic acids (France No. 1,502,538). It is the discovery of this invention, however, that benzoic acids having a phenoxy substituent in the 5-position are very effective herbicides.

SUMMARY OF THE INVENTION

This invention provides herbicidal compounds having the formula:

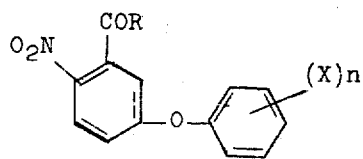

wherein X is a member selected from the group consisting of hydrogen, halogen (e.g., iodine, fluorine, chlorine and bromine), nitro, trifluoromethyl, cyano, COOH,

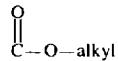

(eg. alkyl of 1 to 4 carbon atoms), hydroxy, alkoxy of 1 to 4 carbon atoms, alkyl of 1 to 4 carbon atoms,

SH, $SR_1$, $SOR_1$, $SO_2R_1$, $SO_2NH_2$ and combinations thereof, $R_1$ and $R_2$ are selected from the group consisting of alkyl of 1 to 4 carbon atoms, R is selected from the group consisting of hydroxy, alkoxy of 1 to 5 carbon atoms, aryloxy, chloro, amido, alkylamido of 1 to 4 carbon atoms, dialkylamido of 2 to 6 carbon atoms, SH, $SR_1$, and OM in which M is an alkali metal (eg., lithium, sodium and potassium), alkylammonium of 1 to 4 carbon atoms or alkanolammonium of 1 to 4 carbon atoms, n is an integer of 1 to 5, and in which compound at least one X is other than hydrogen; their use as herbicides; and a herbicidal composition comprising at least one of said compounds and a carrier therefor.

DESCRIPTION OF SPECIFIC EMBODIMENTS

The compounds of this invention are readily prepared by the Ullmann ether synthesis reaction between the alkali metal, (eg., Na, K) salt of a suitable substituted phenol and a 5-halo (eg., F, Cl, Br)-2-nitrobenzoic acid or an ester, amide, or salt thereof. The 5-halo-2-nitro-benzoic acid or ester is readily prepared by nitrating a m-halotoluene, followed by oxidation of the methyl group by well-known procedures. Also, the m-halobenzoic acid or ester may be directly nitrated by well-known procedures.

Non-limiting examples of the compounds of this invention are:

propyl 2-nitro-5-(2′,4′,6′-tribromophenoxy)benzoate;
phenyl 2-nitro-5-(2′,4′,5′-trifluorophenoxy)benzoate;
2-nitro-5-(2′,4′,6′-triiodophenoxy)benzoic acid;
2-nitro-5-(2′,4′,6′-trichlorophenoxy)benzoyl chloride;
2-nitro-5-(2′,4′,6′-trichlorophenoxy)benzamide;
N-ethyl 2-nitro-5-(2′,4′,6′-trichlorophenoxy)benzamide;
N-isopropyl 2-nitro-5-(2′,4′,6′-trichlorophenoxy)benzamide;
N,N-dimethyl 2-nitro-5-(2′,4′,6′-trichlorophenoxy)benzamide;
ethylammonium 2-nitro-5-(2′,4′,6′-trichlorophenoxy)benzoate;
ethanolammonium 2-nitro-5-(2′,4′,6′-trichlorophenoxy)benzoate;
methyl 2-nitro-5-(2′,3′,4′,5′,6′-pentachlorophenoxy)benzoate;
n-pentyl 2-nitro-5-(2′,4′,6′-trichlorophenoxy)benzoate;
2-nitro-5-(2′,4′-dichlorophenoxy)benzoic acid;
methyl 2-nitro-5-(2′-chlorophenoxy)benzoate;
methyl 2-nitro-5-(4′-chloro-3′-methylphenoxy)benzoate;
methyl 2-nitro-5-(3′-methylphenoxy)benzoate;
ethyl 2-nitro-5-(2′,6′-dichlorophenoxy)benzoate;
isopropyl 2-nitro-5-(2′,4′-dichloro-6′-methylphenoxy)benzoate;
ethyl 2-nitro-5-(2′-chloro-4′-fluorophenoxy)benzoate;
2-nitro-5-(2′-chloro-4′-fluorophenoxy)benzoic acid;
methyl 2-nitro-5-(2′,4′-dinitrophenoxy)benzoate;
2-nitro-5-(2′,4′-dinitrophenoxy)benzoic acid;
2-nitro-5-(2′-chloro-4′-nitrophenoxy)benzoic acid;
isopropyl 2-nitro-5-[3′-(α,α,α-trifluoromethyl)phenoxy]benzoate;
isopropyl 2-nitro-5-[3′,5′-dicarbomethoxyphenoxy]benzoate;
methyl 2-nitro-5-(2′-methoxyphenoxy)benzoate;
methyl 2-nitro-5-(4′-chloro-2′-nitrophenoxy)benzoate;
2-nitro-5-(2′,4′-dichloro-6′-fluorophenoxy)benzoic acid;
methyl 2-nitro-5-(2′,4′-dichloro-6′-fluorophenoxy)benzoate;
methyl 2-nitro-5-(2′,4′-dicarbomethoxyphenoxy)benzoate;
methyl 2-nitro-5-[2′-cyano-4′-(α,α,α-trifluoromethyl)phenoxy]benzoate;
methyl 2-nitro-5-(3′-carbomethoxy-4′-hydroxyphenoxy)benzoate;
methyl 2-nitro-5-[4′-chloro-2′-(α,α,α-trifluoromethyl)phenoxy]benzoate;

methyl 2-nitro-5-(3'-carbomethoxy-4'-nitrophenoxy)-benzoate;

methyl 2-nitro-5-(4'-chloro-2',6'-dibromophenoxy)benzoate;

methyl 2-nitro-5-(2',4'-dicyanophenoxy)benzoate;

methyl 2-nitro-5-[2'-dimethylamino-4'-($\alpha,\alpha,\alpha$-trifluoromethyl)phenoxy]benzoate;

ethyl 2-nitro-5-[2'-amino-4'-($\alpha,\alpha,\alpha$-trifluoromethyl)phenoxy]benzoate;

methyl 2-nitro-5-[2'-methyl-4'-methylthiophenoxy]benzoate;

N,N-dimethyl 2-nitro-5[2',6'-dimethyl-4'-methylthiophenoxy]benzamide;

methyl 2-nitro-5-[2'-methyl-4'-methylsulfonylphenoxy]benzoate;

ethyl 2-nitro-5-[2'-chloro-4'-methylsulfinylphenoxy]benzoate;

methyl 2-nitro-5-[4'-(N-trifluoromethylsulfonamido)phenoxy]benzoate;

methyl 2-nitro-5-(4'-cyanophenoxy)benzoate;
ethyl 2-nitro-5-(4'-carboethoxyphenoxy)benzoate;
methyl 2-nitro-5-(4'-hydroxyphenoxy)benzoate
2-nitro-5-[2'-t-butylphenoxy]benzoic acid;
2-nitro-5-[2'-carboxyphenoxy]benzoic acid;
methyl 2-nitro-5-(4'-aminophenoxy)benzoate;
methyl 2-nitro-5-(4'-diethylaminophenoxy)benzoate;
methyl 2-nitro-5-(2'-methylaminophenoxy)benzoate;
methyl 2-nitro-5-(4'-mercaptophenoxy)benzoate;
ethyl 2-nitro-5-(4'-methylthiophenoxy)benzoate;
methyl 2-nitro-5-(2'-sulfonamidophenoxy)benzoate;
ethyl 2-nitro-5-(4'-methylsulfinylphenoxy)benzoate;
methyl 2-nitro-5-(4'-methylsulfonylphenoxy)benzoate; and
2-nitro-5-(2',4'-dichlorophenoxy)thiobenzoic acid.

The following example illustrates the preparation of a typical compound of this invention and demonstrates a method for product recovery.

EXAMPLE 1

Methyl 2-nitro-5-(2',4',6'-trichlorophenoxy)benzoate

A stirred solution of methyl 5-chloro-2-nitro-benzoate (17.0 g., 0.079 mole) and the potassium salt of 2,4,6-trichlorophenol (18.6 g., 0.079 mole) in dimethyl sulfoxide (100 ml.) was heated at 90°C for 17 hours. The cooled reaction mixture was diluted with water (500 ml.) and then extracted with ether (3 × 100 ml.). The combined ether fractions were washed with 10% sodium hydroxide solution (2 × 30 ml.) and then with a saturated aqueous sodium chloride solution. The ether solution was dried ($Na_2SO_4$) and the solvent evaporated to give a dark oil. Two crystallizations (petroleum ether) gave 1.91 g. of a pale yellow solid, m.p. 101°–103°C.

EXAMPLE 1

IR(nujol): c=o 1723, c-o 1240, and 1260 cm$^{-1}$ NMR (CDCl$_3$): methyl 3.91 ppm (3H), quartet 6.96 ppm (1H, J = 2.5 and 8 c.p.s.), doublet 7.05 ppm (1H, J = 2.5 c.p.s.), broad singlet 7.05 ppm (2H), and doublet 8.01 ppm (1H, J = 8 c.p.s.).

EXAMPLES 2 THROUGH 24

Using procedures similar to that described in Example 1, twenty-three other compounds within the scope of this invention were prepared. These compounds are:

2. 2-nitro-5-(2',4',6'-trichlorophenoxy)benzoic acid, m.p. 184°–189°C.

3. sodium 2-nitro-5-(2',4',6'-trichlorophenoxy)benzoate m.p.>300°C.

4. methyl 2-nitro-5-(2',4',5'-trichlorophenoxy)benzoate m.p. 100°–103°C.

5. methyl 2-nitro-5-(2',4'-dichlorophenoxy)benzoate, m.p. 84°–86°C.

6. ethyl 2-nitro-5-(2',4',6'-trichlorophenoxy)benzoate, m.p. 60°–64°C.

7. methyl 2-nitro-5-(2',4'-dibromophenoxy)benzoate, m.p. 98°–100°C.

8. methyl 2-nitro-5-(4'-chloro-2'-methylphenoxy)benzoate, m.p. 70°–72°C.

9. methyl 2-nitro-5-(2',4'-dimethylphenoxy)benzoate, oil.

10. 2-nitro-5-(2',4'-dichlorophenoxy)benzamide, m.p. 130°–133°C.

11. isopropyl 2-nitro-5-(2',4',6'-trichlorophenoxy)benzoate, m.p. 71°–74°C.

12. ethyl 2-nitro-5-(2',4'-dichlorophenoxy)benzoate, m.p. 83°–85°C.

13. isopropyl 2-nitro-5-(2',4'-dichlorophenoxy)benzoate, m.p. 59°–62°C.

14. methyl 2-nitro-5-(2',4',6'-trichlorophenoxy)thiobenzoate, m.p. 96°–100°C.

15. methyl 2-nitro-5-(2',4'-dichloro-6'-methylphenoxy)benzoate, m.p. 85°–89°C.

16. methyl 2-nitro-5-(2'-chloro-4'-fluorophenoxy)benzoate, m.p. 67°–70°C.

17. isopropyl 2-nitro-5-(2'-chloro-4'-fluorophenoxy)benzoate, m.p. 48°–51°C.

18. N-methyl 2-nitro-5-(2',4'-dichlorophenoxy)benzamide, m.p. 137°C.

19. ethyl 2-nitro-5-(4'-nitrophenoxy)benzoate, m.p. 75°–82°C.

20. methyl 2-nitro-5-(3'-methyl-4'-nitrophenoxy)benzoate, m.p. 75°–82°C.

21. isopropyl 2-nitro-5-[2'-nitro-4'-($\alpha,\alpha,\alpha$-trifluoromethyl)phenoxy]benzoate, oil.

22. ethyl 2-nitro-5-[2'-nitro-4'-($\alpha,\alpha,\alpha$-trifluoromethyl)phenoxy]benzoate, oil.

23. methyl 2-nitro-5-[2'-chloro-4'-nitrophenoxy]benzoate, m.p. 97°–102°C.

24. 2-nitro-5-(2'-chloro-4'-nitrophenoxy)benzoic acid, m.p. 185°C.

EXAMPLE 25

2-Nitro-5-[2'-nitro-4'-($\alpha,\alpha,\alpha$-trifluoromethyl)phenoxy]benzoic acid A stirred solution of 4-chloro-3-nitrobenzotrifluoride (22.55 g, 0.1 mole) and the potassium salt of 3-methyl-4-nitrophenol (19.12 g, 0.1 mole) in dimethyl acetamide (75 ml) was heated at 150° for 4 hours. The cooled reaction solution was diluted with water (300 ml) to precipitate a brown solid which was filtered and dried to give 28.9 g (85%) of 4-nitro-3-tolyl-2'-nitro-$\alpha,\alpha,\alpha$-trifluoro-4'-tolyl ether, which had an m.p. of 82°–85°C. To a stirred solution of the above diphenyl ether product (25.0 g, 0.073 mole) and sodium dichromate (35.8 g, 0.12 mole) in glacial acetic acid (200 ml) was added concentrated sulfuric acid (60 ml, 1.15 moles) over about 30 minutes. The temperature was maintained below 70°C during the addition and then raised to 110°C for 15 hours. The reaction solution was cooled to 60°C and extracted with hot chloroform. The extract was evaporated to dryness to give an oily solid, which was leached free of starting material with an ether-ligroin mixture. The resulting off-white solid acid weighed 13.6 g (51%), m.p. 185°–187°.

EXAMPLE 26

2-Nitro-5-[2'-nitro-4'-($\alpha,\alpha,\alpha$-trifluoromethyl)phenoxy]benzoic acid methyl ester A stirred solution of the acid from Example 6 (3.5 g, 0.0094 mole) in a 25 wt. %/vol. solution of borontrifluoride in methanol (50 ml) was refluxed for 10 hours. The cooled solution was poured onto water (250 ml) and the resulting oil separated and dried to give 3.4 g (93.5%) of the desired product.

COMPARATIVE EXAMPLES

A series of compounds were prepared which are position isomers of the compounds of Example 1 through 4. Each compound is designated by the number of the corresponding isomeric compound of Examples 1 through 4, followed by "a" or "b". These compounds are:

1a. methyl 5-nitro-2-(2',4',6'-trichlorophenoxy)benzoate, m.p. 128°–133°C.

2a. 5-nitro-2-(2',4',6'-trichlorophenoxy)benzoic acid, m.p. 175°–177°C.

2b. 4-nitro-2-(2',4',5'-trichlorophenoxy)benzoic acid, m.p. 190°–193°C.

3a. sodium 5-nitro-2-(2',4',6'-trichlorophenoxy)benzoate, m.p. <300°C.

4a. methyl 5-nitro-2-(2',4',5'-trichlorophenoxy)benzoate, m.p. 104°–106°C.

4b. methyl 4-nitro-2-(2',4',5'-trichlorophenoxy)benzoate, m.p. 127°–131°C.

As is apparent from the data in the Table set forth hereinafter, the compounds embodied herein in which the nitro group is in the 2-position and the substituted phenoxy group is in the 5-position exhibit markedly higher effectiveness as herbicides than do the comparable compounds in which the nitro group and the substituted phenoxy group are in different positions.

The compounds of this invention can be applied in various ways to achieve herbicidal action. They can be applied, per se, as solids or in vaporized form, but are preferably applied as the toxic components in pesticidal compositions of the compound and a carrier. The compositions can be applied as dusts, as liquid sprays, or as gas-propelled sprays and can contain, in addition to a carrier, additives such as emulsifying agents, binding agents, gases compressed to the liquid state, odorants, stabilizers, and the like. A wide variety of liquid and solid carriers can be used. Non-limiting examples of solid carriers include talc, bentonite, diatomaceous earth, pyrophyllite, fullers earth, gypsum, flours derived from cotton seeds and nut shells, and various natural and synthetic clays having a pH not exceeding about 9.5. Non-limiting examples of liquid carriers, include water; organic solvents, such as alcohols, ketones, amides and esters; mineral oils, such as kerosene, light oils, and medium oils and vegetable oils, such as cottonseed oil.

In practice, herbicidal application is measured in terms of pounds of herbicide applied per acre. The compounds of this invention are effective herbicides when applied in herbicidal amounts, i.e., at rates between about 0.2 pounds and about 10 pounds per acre.

HERBICIDAL EFFECTIVENESS

Method of Propagating Test Species

| | |
|---|---|
| Crabgrass | *Digitaria sanguinalis* |
| Yellow Foxtail grass | *Setaria glauca* |
| Johnson grass | *Sorgum Halepense* |
| Barnyard grass | *Echinochloa crus-galli* |
| Amaranth pigweed | *Amaranthus retroflexus* |
| Turnip | *Brassica sp.* |
| Cotton | *Gossypium hirsutum* var. DPL smooth leaf |
| Corn | *Zea Mays* var. Golden Bantam |
| Bean | *Phaseolus vulgaris* var. Black Valentine |

All crop and weed species are planted individually in 3 inch plastic pots containing potting soil. Four seeds of each of corn, cotton, and snapbeans are seeded to a depth equal to the diameter of the seed. All other species are surface seeded and sprinkled with screened soil in an amount sufficient to cover the seeds. Immediately after planting, all pots are watered by sub-irrigation in greenhouse trays. Pots for the pre-emergence phase are seeded one day before treatment.

Planting dates for the post-emergence phase are varied so that all the seedlings will reach the desired state of development simultaneously. The proper state of seedling development for treatment in the post-emergence phase is as follows:

| | |
|---|---|
| GRASSES: | 2 inches in height |
| PIGWEED & TURNIPS: | 1 or 2 true leaves visible above cotyledons. |
| COTTON: | first true leaf 1 inch in length; expanded cotyledons. |
| CORN: | 3 inches – 4 inches in height |
| BEANS: | primary leaves expanded, growing point at primary leaf node. |

Method of Treatment

Spray applications are made in a hood containing movable belt and fixed spray nozzle. For passage through the spray hood, one pot of each species (pre-emergence phase) is placed on the forward half of a wooden flat and one pot of established plants (post-emergence phase) is placed on the rear half of the flat. Treatments are moved to the greenhouse after spraying. Watering during the observation period is applied only by sub-irrigation.

Compounds are screened initially at a rate of application equivalent to four or eight pounds per acre. Two weeks after treatment the pre- and post-emergence percent effectiveness is visually rated. Subsequent testing is carried out at 2, 1 and 0.5 pounds per acre.

Herbicidal testing of the compounds of Examples 1 through 7 and of the comparative compounds provided the results set forth in the Table. The plants are tabulated using the following abbreviations:

| | | | |
|---|---|---|---|
| Crabgrass | CG | Pigweed | PW |
| Yellow Foxtail grass | YF | Turnip | TP |
| Johnson grass | JG | Cotton | CT |
| Barnyard grass | BG | Corn | CN |
| Bean | BN | | |

TABLE

PRE/POST-EMERGENCE HERBICIDAL ACTIVITY* OF CERTAIN SUBSTITUTED PHENOXYBENZOIC ACIDS AND DERIVATIVES THEREOF

| COMPOUND OF EXAMPLE | COMPOUND CONCENTRATION, LBS./ACRE | CG | YF | JG | BG | PW | TP | CT | CN | BN |
|---|---|---|---|---|---|---|---|---|---|---|
| 1 | 4 | 100/100 | 100/100 | 60/50 | 60/70 | 100/100 | 80/100 | 0/100 | 0/40 | 30/100 |
|  | 2 | 100/100 | 80/100 | 30/70 | 20/80 | 100/100 | 0/100 | 90/100 | 30/20 | 70/100 |
|  | 1 | 100/90 | 80/100 | 20/60 | 0/60 | 100/100 | 30/90 | 0/100 | 0/20 | 80/100 |
|  | 0.5 | 40/50 | 60/80 | 30/60 | 0/40 | 100/70 | 0/80 | 40/20 | 0/20 | 30/70 |
| 1a(Comparative) | 4 | 20/20 | 0/20 | 0/20 | 0/20 | 20/0 | 0/30 | 100/0 | 50/0 | 20/80 |
| 2 | 4 | 70/70 | -/- | 70/90 | 60/70 | -/- | 100/100 | 0/100 | 0/70 | 80/70 |
| 2a(Comparative) | 4 | 20/30 | 0/20 | 20/30 | 0/20 | -/20 | 30/90 | 50/20 | 0/0 | 50/70 |
| 2b(Comparative) | 4 | 0/30 | 40/0 | 50/30 | 20/20 | 20/20 | 0/50 | 40/20 | 30/30 | 80/0 |
| 3 | 4 | 50/80 | -/- | 30/60 | 40/60 | -/- | 95/100 | 50/100 | 0/40 | 50/100 |
| 3a(Comparative) | 4 | 0/20 | 0/20 | 0/20 | 0/20 | 50/50 | 0/60 | 100/0 | 30/0 | 50/40 |
| 4 | 4 | 90/60 | -1- | 80/90 | 50/50 | -/- | 40/70 | 80/70 | 0/50 | 80/80 |
| 4a(Comparative) | 8 | 30/30 | 0/20 | 20/30 | 0/20 | 30/30 | 40/0 | 0/30 | 0/0 | 60/0 |
| 4b(Comparative) | 4 | 20/20 | 0/20 | 0/20 | 0/20 | 0/20 | 0/60 | 30/50 | 0/30 | 0/60 |
| 5 | 4 | 100/95 | -/- | 90/90 | 90/90 | -/- | 80/100 | 50/80 | 0/40 | 50/100 |
| 6 | 4 | 100/80 | -/- | 80/50 | 50/70 | 100/100 | 40/90 | 30/100 | 0/100 | 100/100 |
| 7 | 8 | 80/60 | -/- | 50/40 | 60/50 | 100/100 | 20/100 | 30/90 | 0/50 | 100/100 |
| 8 | 8 | 50/60 | -/- | 20/30 | 0/20 | 100/100 | 0/40 | 0/40 | 0/30 | 100/100 |
| 9 | 8 | 30/30 | -/- | 0/40 | 20/20 | 90/90 | 20/50 | 0/70 | 0/40 | 100/90 |
| 10 | 4 | 80/70 | -/- | 40/40 | 40/30 | 100/100 | 20/70 | 100/40 | 0/20 | 100/100 |
| 11 | 4 | 60/70 | -/- | 30/60 | 20/50 | 90/100 | 0/50 | 30/70 | 0/30 | 80/60 |
| 12 | 8 | 90/90 | -/- | 90/90 | 60/70 | 100/100 | 0/100 | 0/100 | 0/70 | 0/100 |
|  | 4 | 100/90 | -/- | 90/100 | 60/60 | 100/100 | 0/100 | 30/90 | 0/70 | 30/100 |
|  | 2 | 100/100 | 100/- | 40/60 | 80/70 | -/100 | 30/100 | 80/70 | 0/70 | 100/100 |
|  | 1 | 100/100 | -/- | 40/90 | 50/80 | -/- | 30/100 | 20/80 | 0/20 | 50/80 |
| 13 | 8 | 70/90 | -/- | 30/90 | 20/80 | 90/100 | 0/30 | 30/70 | 0/20 | 100/100 |
| 14 | 4 | 70/80 | -/- | 20/90 | 0/40 | 100/100 | 70/100 | 90/90 | 20/20 | 0/80 |
| 15 | 8 | 100/100 | 100/- | 50/70 | 50/- | -/100 | 70/90 | 0/90 | 0/30 | 50/100 |
|  | 4 | 90/90 | 0/- | 40/60 | 0/60 | -/- | 60/90 | 100/60 | 0/40 | 0/100 |
|  | 2 | 90/70 | -/- | 30/40 | 20/70 | -/- | 70/60 | 0/60 | 0/50 | 0/100 |
| 16 | 8 | 100/90 | 100/100 | 80/100 | 100/90 | 100/100 | 100/100 | 40/100 | 80/40 | 80/100 |
|  | 4 | 100/100 | 100/100 | 100/100 | 80/80 | 100/100 | 70/100 | 40/90 | 20/80 | 80/100 |
|  | 2 | 100/100 | 100/100 | 90/100 | 80/90 | 100/100 | 80/100 | 30/90 | 0/80 | 0/90 |
|  | 0.8 | 90/60 | 100/80 | 70/50 | 40/50 | 100/100 | 40/100 | 80/60 | 30/20 | 50/100 |
| 17 | 8 | 100/40 | 90/40 | 70/40 | 50/30 | 100/100 | 0/60 | 0/80 | 0/30 | 0/90 |
|  | 4 | 100/90 | 100/100 | 80/90 | 50/70 | 100/100 | 0/40 | 0/50 | 0/30 | 0/90 |
|  | 2 | 100/90 | 100/90 | 30/90 | 30/90 | 100/100 | 20/30 | 0/50 | 0/30 | 0/90 |
|  | 1 | 60/50 | 100/80 | 90/60 | 20/30 | 100/100 | 0/40 | 90/30 | 30/0 | 80/80 |
| 18 | 8 | 90/80 | -/- | 60/80 | 70/40 | -/- | 90/100 | 30/80 | 0/80 | 0/100 |
| 19 | 10 | 40/30 | -/- | 90/- | -/- | -/- | 0/90 | -/60 | -/- | -/60 |
| 20 | 10 | 50/20 | -/- | 90/- | -/- | -/- | 20/20 | -/30 | -/- | -/40 |
| 21 | 3 | 100/- | 100/- | 100/-/ | 30/- | -/- | 50/- | 30/- | 0/- | 0/- |
| 22 | 1 | 90/- | 100/- | 100/- | 30/- | -/- | 30/- | 50/- | 60/- | 0/- |
| 23 | 10 | 80/- | 100/- | 100/- | 30/- | -/- | 80/- | -/- | -/- | -/- |
| 24 | 10 | 100/- | -/- | 30/- | -/- | -/- | 100/- | -/- | -/- | -/- |
| 25 | 8 | 80/60 | 90/100 | 50/40 | 30/60 | 100/100 | 100/100 | 30/50 | 0/30 | 30/90 |
| 26 | 8 | 100/80 | 100/90 | 40/20 | 90/60 | 100/100 | 90/90 | 0/50 | 0/20 | 70/90 |
|  | 4 | 100/90 | 100/100 | 70/90 | 80/50 | 100/100 | 100/100 | 0/50 | 0/20 | 0/90 |
|  | 2 | 90/70 | 100/100 | 60/60 | 40/70 | 100/100 | 90/90 | 0/50 | 0/30 | 0/90 |

*Herbicidal activity is measured in per cent effectiveness

Although the present invention has been described with preferred embodiments, it is to be understood that modifications and variations may be resorted to without departing from the spirit and scope of this invention, as those skilled in the art will readily understand. Such modifications and variations are considered to be within the purview and scope of the appended claims.

What is claimed is:

1. A compound having the formula:

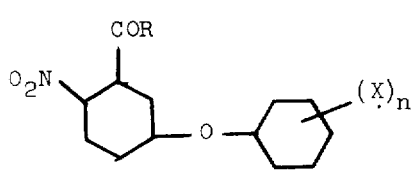

wherein X is halogen, $C_1$-$C_4$ alkyl, or $NO_2$ and at least one X is halogen and another is $C_1$-$C_4$ alkyl or $NO_2$; R is hydroxy or alkoxy of 1 to 5 carbon atoms; and n is 2 to 5.

2. A compound of claim 1, wherein said compound is methyl 2-nitro-5-(2',4'-dichloro-6'-methylphenoxy)-benzoate.

3. A compound of claim 1, wherein said compound is methyl 2-nitro-5-(4'-chloro-2'-methylphenoxy)benzoate.

4. A compound of claim 1, wherein said compound is methyl 2-nitro-5-(2'-chloro-4'-nitrophenoxy)benzoate.

5. A compound of claim 1, wherein said compound is 2-nitro-5-(2'-chloro-4'-nitrophenoxy)benzoic acid.

* * * * *

UNITED STATES PATENT AND TRADEMARK OFFICE
CERTIFICATE OF CORRECTION

PATENT NO. : 3,941,830
DATED : March 2, 1976
INVENTOR(S) : Robert J. Theissen

It is certified that error appears in the above—identified patent and that said Letters Patent are hereby corrected as shown below:

In Claim 1,

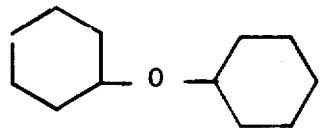

should read

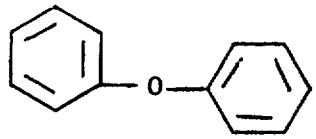

Signed and Sealed this

Thirtieth Day of January 1979

[SEAL]

Attest:

RUTH C. MASON
Attesting Officer

DONALD W. BANNER
Commissioner of Patents and Trademarks

REEXAMINATION CERTIFICATE (217th)

United States Patent [19]

Theissen

[11] B1 3,941,830

[45] Certificate Issued Jul. 17, 1984

[54] SUBSTITUTED PHENOXYBENZOIC ACIDS AND ESTERS THEREOF

[75] Inventor: Robert J. Theissen, Westfield, N.J.

[73] Assignee: Rhone-Poulenc Agrochemie, Lyon, France

Reexamination Request:
No. 90/000,278, Oct. 28, 1982

Reexamination Certificate for:
Patent No.: 3,941,830
Issued: Mar. 2, 1976
Appl. No.: 398,610
Filed: Sep. 19, 1973

Related U.S. Application Data

[63] Continuation of Ser. No. 114,712, Feb. 11, 1971, Pat. No. 3,784,635, which is a continuation-in-part of Ser. No. 819,412, Apr. 25, 1969, Pat. No. 3,652,645.

[51] Int. Cl.$^3$ .............................................. C07C 69/78
[52] U.S. Cl. ...................................... 560/21; 562/435; 71/114
[58] Field of Search .................. 560/21; 562/435, 437

[56] References Cited

U.S. PATENT DOCUMENTS 3,316,080  4/1967  Inoue et al. ............................ 71/2.3
3,423,470  1/1969  Rohr et al. ............................ 260/612

OTHER PUBLICATIONS

Fults, et al., "A Biometric Evaluation of the Growth-Regulating and Herbicidal Properties of Some Organic Compounds", *Journal of American Society of Agronomy*, 1947, pp. 667–681.

*Primary Examiner*—Paul J. Killos

[57] ABSTRACT

2-Nitro-5-(substituted-phenoxy)benzoic acids and esters salts, amides, and acyl halides thereof comprise a class of compounds that are highly effective herbicides.

REEXAMINATION CERTIFICATE ISSUED UNDER 35 U.S.C. 307.

THE PATENT IS HEREBY AMENDED AS INDICATED BELOW.

AS A RESULT OF REEXAMINATION, IT HAS BEEN DETERMINED THAT:

Claims 1–5 are cancelled.

* * * * *